United States Patent [19]

Krämer et al.

[11] 4,247,643

[45] Jan. 27, 1981

[54] PREPARATION OF STABILIZED CARRIER-BOUND PROTEINS

[75] Inventors: Dieter Krämer, Mainz; Klaus Sauber, Bad Soden, both of Fed. Rep. of Germany

[73] Assignee: Röhm GmbH Chemische Fabrik, Darmstadt, Fed. Rep. of Germany

[21] Appl. No.: 924,346

[22] Filed: Jul. 13, 1978

[30] Foreign Application Priority Data

Jul. 16, 1977 [DE] Fed. Rep. of Germany ....... 2732301

[51] Int. Cl.$^3$ ...................... C12N 11/10; C12N 11/08; C12N 9/96

[52] U.S. Cl. ........................................ 435/178; 435/44; 435/180; 435/188; 435/230; 260/112 R

[58] Field of Search .................. 195/63, 68, DIG. 11; 435/177, 178, 180, 181, 188, 44, 230; 260/112 R

[56] References Cited

U.S. PATENT DOCUMENTS

| | | | |
|---|---|---|---|
| 3,645,852 | 2/1972 | Axon et al. .............................. | 195/68 |
| 3,853,708 | 12/1974 | Porath et al. .......................... | 195/68 |
| 4,008,126 | 2/1977 | Keyes .................................. | 195/68 X |

OTHER PUBLICATIONS

Cleland, W. W. Dithiothreitol, A New Protective Reagent for SH Groups, Biochemistry, vol. 3, No. 4 1964, pp. (480–482).

Konigsberg, W. Reduction of Disulfide Bonds in Proteins with Dithiothreitol Methods in Enzymology, vol. XXXV, 1972 (pp. 185–188).

*Primary Examiner*—David M. Naff
*Attorney, Agent, or Firm*—Oblon, Fisher, Spivak, McClelland & Maier

[57] ABSTRACT

Stabilized carrier-bound protein is prepared by reacting a protein in aqueous solution with a mercapto group free, water insoluble carrier which contains binding groups which are reactive with the said protein and reacting the resultant protein-containing mercapto group-free carrier with hydrogen sulfide or with a compound having a molecular weight of less than 5000, and which contains at least two mercapto groups, or at least one mercapto group and at least one hydroxy- group or primary or secondary amino group.

14 Claims, No Drawings

PREPARATION OF STABILIZED CARRIER-BOUND PROTEINS

FIELD OF THE INVENTION

This invention relates to a method for the preparation of stabilized carrier-bound proteins.

BACKGROUND OF THE INVENTION

Description of the Prior Art

In methods which depend on the biospecific effect between proteins and their corresponding substrates, it is advantageous to use the proteins in the form of a solid carrier-bound or immobilized form. The proteins can thus be separated from the substrate solution quite easily by filtration. Carrier-bound proteins have importance in affinity chromatography and especially in the carrying out of enzymatic processes, wherein the carrier-bound protein is an enzyme.

Carrier-bound proteins are generally characterized by higher stability against inactivation due to shifts in pH values, higher temperatures and higher stability against autooxidation as compared with free proteins in aqueous solution. Nevertheless, a decrease in the biospecific activity—such as in the case of enzymes the enzymatic activity—is observed after multiple uses of the carrier-bound proteins.

It is known that one can stop, or even decrease, the activity loss of proteins by treatment with various mercaptans (see for example Dissertation of Jan Carlsson, Uppsala, 1974, page 8, Abstract). The effectiveness of the mercaptans is presumed to be a result of their ability to split disulfide bridges which resulted by autooxidation of thiol groups. Autooxidation is thus generally seen as the cause of the reversible loss in activity.

In most cases, however, it is not desirable to add a mercaptan to a substrate solution to maintain the activity of bound proteins, since to do so would adversely affect the purity of the substrate solution, and would require a purification step. Separate reactivation of carrier-bound proteins between successive runs is generally not satisfactory since it encompases additional expense and most mercaptans are toxic and foul-smelling.

SUMMARY OF THE INVENTION

Accordingly, it is one object of this invention to prepare carrier-bound proteins with increased stability.

Another object of the invention is to prepare carrier-bound proteins which are not subject to activity losses in aqueous solution caused by repeated use and which are prepared by reaction of the protein with a water insoluble carrier material.

These and other objects of the invention which will hereinafter become apparent from the following description, have now been achieved by reacting a protein-containing mercapto group-free carrier with hydrogen sulfide or a compound with a molecular weight under 5000, preferably under 2000, which contains at least two mercapto groups or at least one additional mercapto-, and at least one additional hydroxy-, primary or secondary amino group.

DESCRIPTION OF THE PREFERRED EMBODIMENTS

Since it has been assumed by those skilled in this art that the stabilizing effect of mercaptans depends on their reaction with disulfide bridges, it is quite unexpected to now discover that such groups also are effective when bound to the carrier material, where they are incapable of being in physical proximity with the disulfide bridges. Contrary to expectations, it has now been discovered that it is possible to achieve an increased stabilization through mercapto groups bound to the carrier. In the following table the loss in activity upon multiple repeated use of a carrier-bound penicillin-acylase, with and without mercapto groups bound on the carrier is described. The mercapto groups were introduced in this case through binding of dithiothreitol to any epoxy group-containing enzyme carrier. The carrier material was a cross-linked acrylamido polymer with epoxy groups, which was first reacted with penicillin-acylase and thereafter with 50 or 500 mg dithiothreitol per gram of moist carrier material. The activity of the preparation against penicillin G (potassium salt) was tested during repeated reactions using between one and two grams of the preparation with about 5 percent substrate and 200 ml substrate solution (0.01 M phosphate buffer, pH 7.5) at 37° C. by means of an automatic titration with 1.0 N NaOH. The starting activity during the first utilization was denoted as 100 percent.

| Number of the Utilizations | Activity as Percent of Starting Activity | | |
| --- | --- | --- | --- |
| | Without Mercaptan | With 50 mg Dithiothreitol | With 500 mg Dithiothreitol |
| 1 | 100 | 100 | 100 |
| 2 | 96 | 100 | 100 |
| 3 | 89 | 99 | 98 |
| 4 | 85 | 96 | 98 |
| 5 | 76 | 96 | 98 |
| 6 | 75 | 96 | 96 |
| 7 | 69 | 97 | 95 |
| 8 | 65 | 96 | 92 |
| 9 | 64 | 96 | 95 |
| 10 | 64 | — | 95 |
| 11 | 61 | 84 | 95 |
| 12 | 56 | 79 | 93 |
| 15 | 52 | 75 | 93 |
| 20 | 43 | 65 | 89 |
| 25 | 34 | 58 | 75 |

The achieved stability brought about by this invention depends on the binding of hydrogen sulfide or of a compound which contains at least two mercapto groups or at least one mercapto- group and at least one hydroxy- group, or primary or secondary amino group onto the reactive groups of the carrier material. The mercapto-, hydroxy- or amino groups of the above-mentioned compounds react with the reactive groups of the carrier material in the same fashion as the corresponding groups of the bound proteins. Since the molecular weight of these above-mentioned compounds is under 5000, it is possible for them, due to their small molecular size, to react with reactive groups on the carrier material which are unapproachable to protein molecules due to steric hinderence resulting from the latter's larger size. The reactive groups on the carrier, react faster with hydrogen sulfide or with mercapto-, hydroxy- and amino groups than with water. It is thus possible to carry out both the reaction of the reactive groups of the carrier with the protein as well as the further reaction with the mercapto-group containing compound in aqueous phase. Since the reactive groups of the carrier are gradually decomposed by water, it is important to avoid any longer period of time than is necessary between the first and the second reaction steps in the method of the present invention.

The desired stability effect occurs when at least one mercapto group per bound molecular remains in free form and the additional mercapto- hydroxy- or amino groups reacts with the reactive binding active groups of the carrier. The mercapto group-containing compound will predominantly be bound to the carrier by only one of its functional groups, since the carrier is an insoluble solid matrix and has relatively small molecular motions. When this above-mentioned group is an hydroxyl- or an amino group, it is, in any case, possible to preserve a free mercapto group. Upon utilization of a compound with only one mercapto group and one or more amino- or hydroxy groups it might be possible that the mercapto group will react with the binding active group of the carrier, so that only amino- or hydroxy groups remain free. In this case, the bound molecule does not lead to a stabilization effect. Since part of the molecules do not react through the mercapto group but through an amino- or a hydroxy group, there always is a statistically sufficient number of stabilizing mercapto groups that remains free.

The mercapto group-containing compound is in general applied in such amounts that at least 0.3% by weight relative to the moist weight of the carrier-enzyme-product is available as free SH- groups. Hydrogen sulfide and compounds with two or more mercapto groups contain two (or more) sulphur-bound hydrogen atoms, so that after their binding to the carrier there is, in any case, one free remaining mercapto group. Compounds with two or more SH- groups are particularly preferred. Compounds of this group include dithioethyleneglycol, dithiopropyleneglycol or dithiobutyleneglycol, 1,12-dimercaptododecane, the di-mercaptoacetic esters of ethyleneglycol, dodecandiol, neopentylglycol or of 2,2'-bis-(4-hydroxy-cyclohexyl)-propane, trimethylolpropan-tri-mercaptopropionate, pentaerythritol-tetra-mercaptoacetate, -tetra-mercaptopropionate, -tetra-mercaptocaproic ester or -tetra-mercaptoundecanoic acid ester as well as compounds with additional functional groups, such as dithiothreitol. Compounds with one amino- and one mercapto group include mercaptoethylamine and cysteine. Compounds with only one mercapto- and one or more hydroxy groups are at least preferred, since the mercapto groups react as a rule easier than the hydroxy groups with the binding active groups of the carrier. Examples of these types of compounds are monothiolethylenglycol and monothiolpropylenglycol.

A large number of water insoluble carrier materials containing binding active groups which will react with proteins is known. An over view of these carriers and their active groups can be found in O. Zaborsky, "Immobilized Enzymes," Cleveland 1973. As important carrier materials are named therein synthetically cross-linked polymers based on acrylamide, maleic acid anhydride, methacrylic acid, styrene or polypeptides. As naturally occurring carriers are named carbohydrates, such as agarose, cellulose, cross-linked dextrin or starch. Glass and other inorganic materials can also be used as carriers. As binding active groups present in the activated carriers it is possible to use, for example, nitroarylfluoride-, silylchloride-, carbonic acid anhydride, carbonyl-, imidocarbonate; isothiocyanate-, (nitro-)phenylester-, acylazid-, aryldiazonium- or s-triazinyl groups. Methods for the introduction of these groups into the carrier materials are named in Zaborsky as well as in the literature citations individually named therein. The number of binding active groups has to be large enough, so that at least 10 mg, preferably 100 mg or more of protein can be bound per gram of carrier material.

The stabilizing effect is particularly effective in carriers that contain oxirane or amidocarbonate groups as the binding active groups. Oxirane groups can readily be introduced during the preparation of a cross-linked acrylamido polymer, preferably into polymer beads obtained by inverse emulsion polymerization, through the co-utilization of gylcidyl group-containing comonomers, such as gylcidylacrylate or -methacrylate. For carriers with carbohydrate structure such as cellulose, agarose or dextrin, it is possible to introduce glycidyl groups for example through the reaction with epichlorohydrin or 1,4-bis-(2,3-epoxypropyl)-butane. By reacting polysaccharide carriers with cyanogen bromide, it is possible to obtain amidocarbonate groups. It is especially preferred to use bead-shaped carriers with bead cross sections of from 5 to 5000 m$\mu$ because of their ease of manipulation and their easy through-flow properties.

The type of proteins used in this invention, of course, is determined by the intended use and purpose of the ultimate product. For the purposes of affinity chromatography, for example, it is useful to bind a protein carrier which can select one component of a substrate mixture which is to be separated, through biospecific exchange effects. The present invention is particularly well adapted for immobilized enzymes, such as for example penicillin acylase, ribonuclease, amylase or catalase. The only exception is that certain enzymes are sensitive to hydrogen sulfide or mercaptans; and such enzymes would not be used in this invention. Enzymes which can be stabilized or reactivated by use of hydrogen sulfide or free mercaptans, on the other hand, can be effectively stabilized by the methods of this invention.

Having now generally described the invention, a further understanding thereof can be obtained by reference to the following examples, which are included for purposes of illustration only and should not be construed as being limitative of the invention.

EXAMPLE 1

(a) Preparation of Oxirane acrylic resin beads

To a round bottom flask (6000 ml), equipped with a thermometer, mechanical stirrer, reflux condenser, and nitrogen inlet were added:
1740 g n-Heptane
1100 g perchloroethylene
2 g polymer of the composition
 95% n-butylmethacrylate
 5% 2-trimethylammoniumethylmethacrylate chloride;

A nitrogen atmosphere was provided and the temperature was maintained at 55° C. A further mixture of
791 g formamide
60 g methacrylamide
60 g allylglycidyl ether
60 g glycidylmethacrylate
120 g methylene-bis-methacrylamide
6 g benzoylperoxide;

was added with stirring to obtain distribution into the organic phase. The polymerization was accelerated by the addition of 6 g of dimethyl-aniline. After 10 hours of polymerization, the reaction was cooled to room temperature, the beads were allowed to settle and the supernatant liquid phase was decanted. The beads were shrunk by the addition of about 2000 ml of acetone, filtered by suction and washed twice with acetone. In addition they were dried under vacuum at room temperature overnight. Yield: about 90% fine, lightly yellowish beads.

(b) Immobilization of the penicillin acylase 1.2 g penicillin acylase (*E. coli*, specific activity 12.1 U/mg) was dissolved in 40 ml 0.1 M phosphate buffer (pH 8, 0.02% $NaN_3$) and added to 10 grams of product (1a). The reaction mixture was allowed to stand at 23° C. for 72 hours and then washed three times with about 1000 ml 1 N aqueous NaCl-solution and twice with 0.05 M phosphate buffer (pH 7.5; 0.02% $NaN_3$). Yield: 37 g of moist product (after suction filtration on fritted glass). Enzymatic activity: 237 U/g of moist product.

(c) Determination of the activity 2 g of penicillin G (sodium salt) were dissolved in 90 ml phosphate buffer (pH 7.5; 0.05 M) and the volume was brought with this buffer to 100 ml.

20 ml of this substrate solution and 250 mg (moist weight) of the product (1b) were stirred in a titration apparatus thermostated at 37° C. (TTA3, Fa. Radiometer, Copenhagen). The phenylacetic acid set free through hydrolysis was titrated automatically at pH 7.8 with 1 N NaOH from an autoburette (ABU 12, Fa. Radiometer Copenhagen), controlled by a pH-meter and titrator (type 11, Fa. Radiometer, Copenhagen). The sodium hydroxide consumption was simultaneously registered with the aid of a recorder (Titrigraph SBR 2c Fa. Radiometer, Copenhagen).

The activity was obtained from the linear initial range of the graphed reaction curve; one enzyme unit (U) corresponding to one micromole of split substrate per minute.

(d) Activity loss upon repeated use at a 95% turnover rate of substrate solutions of a concentration of 5%

2.0 g of the product (1b) and 20 ml of a 5% substrate solution (5% penicillin-G-K in 0.01 M phosphate buffer, pH 7.5, containing 0.02% $NaN_3$) were stirred at pH 7.5 and 37° C. up to a substrate turnover of 95–98%. The apparatus and recording the reaction curve are described under (1c).

The enzyme beads were then filtered by suction on a fritted glass. and were readded to fresh 20 ml substrate solutin. This procedure was repeated sequentially 20 times.

Activity loss after 20 utilizations: 57%

EXAMPLE 2

2 g of the carrier-bound penicillin acylase according to Example 1(b) were added to 10 ml of an aqueous solution of dithioglycol (2%, brought to pH 7.5 with NaOH). The mixture was allowed to stand at 37° C. for 18 hours and washed with water (10 times about 100 ml) and twice with 0.05 M phosphate buffer (pH 7.5).

Yield: 1.95 g moist product.

The product was tested as in Example 1(d).

Activity loss after 20 repeated utilizations: 42%.

EXAMPLE 3

50 mg of 1,4-dithiothreitol were dissolved in 1 ml $H_2O$ and the pH was adjusted by addition of NaOH to 7.5. The solution was added to 2 g of carrier-bound penicillin acylase according to Example 1(b) and the reaction was allowed to stand for 48 hours at 23° C. It was then washed with water (5 times) and buffer (twice).

Yield: 1.98 g

Activity loss after 20 repeated utilizations, carried out as in Example 1(d): 35%.

EXAMPLE 4

500 mg dithiothreitol was dissolved in 5 ml water and through the addition of NaOH was brought to a pH of 7.8. This solution was then added to 2 g of the carrier-bound penicillin acylase according to Example 1(b) and the reaction mixture was allowed to stand for 48 hours at 23° C. It was then washed with water (5 times) and buffer (twice).

Activity loss after 20 repeated utilizations, carried out according to Example 1(d): 11%.

Having now fully described the invention, it will be apparent to one of ordinary skill in the art that many changes and modifications can be made thereto without departing from the spirit or scope of the invention as set forth herein.

What is new and intended to be claimed and protected by Letters Patent of the United States is:

1. A method for the preparation of a stabilized carrier-bound protein which comprises:
    reacting a protein in an aqueous solution with a portion of the oxirane groups of an oxirane group-containing water insoluble carrier which contains no mercapto groups, to form a protein-containing complex;
    reacting said protein-containing complex with hydrogen sulfide or a compound having a molecular weight less than 5000 which contains at least two mercapto groups; thereby
    attaching to the remaining oxirane groups of said carrier at least 0.3% by weight of free mercapto groups with respect to the moist weight of the end product.

2. A method for the preparation of a stabilized carrier-bound protein which comprises:
    reacting a protein in an aqueous solution with a portion of the oxirane groups of an oxirane group-containing water insoluble carrier which contains no mercapto groups, to form a protein-containing complex;
    reacting said protein-containing complex with a compound with molecular weight less than 5000 which contains at least two mercapto groups; thereby
    attaching to the remaining oxirane groups of said carrier at least 0.3% by weight of free mercapto groups with respect to the moist weight of the end product.

3. A method for the preparation of a stabilized carrier-bound protein which comprises:
    reacting a protein in an aqueous solution with a portion of the oxirane groups of an oxirane group-containing water insoluble carrier which contains no mercapto groups to form a protein-containing complex;
    reacting said protein-containing complex with hydrogen sulfide or a compound having a molecular weight less than 5000 which contains at least two mercapto groups; thereby
    attaching to the remaining oxirane groups of said carrier at least 0.3% by weight of free mercapto groups with respect to the moist weight of the end product; and subsequently extensively washing said carrier-bound protein with water or an aqueous solution.

4. The method of any of claims 1, 2 or 3, wherein said carrier material is prepared from a polyacrylamide or a carbohydrate derivative.

5. The method of any of claims 1, 2 or 3, wherein said carrier material is a bead-shaped carrier with a bead cross-section of between 5 and 1000 μm formed from a cross-linked polyacrylamide.

6. The method of any of claims 1, 2 or 3, wherein said compound with molecular weight of less than 5000 is an aliphatic compound having 2 to 8 C-atoms.

7. The method of any of claims 1, 2 or 3, wherein said bound protein is an enzyme.

8. The method of claim 7, wherein said enzyme is penicillin acylase.

9. The method of any of claims 1, 2 or 3, wherein the molecular weight of said mercapto group containing compound is below 2000.

10. The stabilized carrier bound protein prepared by the process of any of claims 1, 2 or 3.

11. The stabilized carrier bound protein of claim 10, wherein said carrier material is based on a polyacrylamide or carbohydrate derivative.

12. The stabilized carrier bound protein of claim 10, wherein said carrier is in the form of a bead of 5 to 1000 um cross-section.

13. The stabilized carrier bound protein of claim 10, wherein said protein is an enzyme.

14. The stabilized carrier bound protein of claim 13, wherein said enzyme is penicillin acylase.

* * * * *